(12) United States Patent
Varanasi et al.

(10) Patent No.: US 8,030,030 B2
(45) Date of Patent: Oct. 4, 2011

(54) BIOMASS PRETREATMENT

(75) Inventors: Sasidhar Varanasi, Toledo, OH (US); Constance Ann Schall, Sylvania, OH (US); Anantharam Prasad Dadi, Toledo, OH (US); Jared Anderson, Toledo, OH (US); Kripa Rao, Toledo, OH (US); Guneet Kumar, Ellicot City, MD (US); Praveen Paripati, Reston, VA (US)

(73) Assignees: The University of Toledo, Toledo, OH (US); Suganit Systems, Inc., Reston, VA (US)

( * ) Notice: Subject to any disclaimer, the term of this patent is extended or adjusted under 35 U.S.C. 154(b) by 0 days.

(21) Appl. No.: 12/075,762

(22) Filed: Mar. 13, 2008

(65) Prior Publication Data
US 2008/0227162 A1   Sep. 18, 2008

Related U.S. Application Data

(60) Provisional application No. 60/894,708, filed on Mar. 14, 2007.

(51) Int. Cl.
*C12P 19/00* (2006.01)
(52) U.S. Cl. ............. 435/72; 435/41; 435/200; 435/209
(58) Field of Classification Search .................... 435/72, 435/41, 200, 209
See application file for complete search history.

(56) References Cited

U.S. PATENT DOCUMENTS

| 1,943,176 | A | 1/1934 | Graenacher | |
|---|---|---|---|---|
| 2,990,233 | A | 6/1961 | Pacsu | |
| 4,174,976 | A | 11/1979 | Tsao | |
| 4,260,685 | A | 4/1981 | Pilipski | |
| 4,968,350 | A | 11/1990 | Bindschaedler | |
| 5,372,939 | A | 12/1994 | Lastick et al. | |
| 5,916,780 | A | 6/1999 | Foody | |
| 6,808,557 | B2 | 10/2004 | Holbrey et al. | |
| 6,824,599 | B2 | 11/2004 | Swatloski et al. | |
| 7,049,485 | B2 | 5/2006 | Sticklen et al. | |
| 7,674,608 | B2 | 3/2010 | Varanasi et al. | |
| 2004/0053373 | A1* | 3/2004 | Foody et al. | 435/105 |
| 2005/0288484 | A1 | 12/2005 | Holbrey | |
| 2007/0006774 | A1 | 1/2007 | Rogers | |
| 2007/0199613 | A1* | 8/2007 | Bouldin et al. | 141/73 |
| 2007/0215300 | A1 | 9/2007 | Upfal | |
| 2007/0231918 | A1* | 10/2007 | Zeng | 436/141 |
| 2008/0023162 | A1* | 1/2008 | Myllymaki et al. | 162/163 |
| 2008/0164440 | A1 | 7/2008 | Maase | |
| 2008/0185112 | A1 | 8/2008 | Argyropoulos | |
| 2008/0188636 | A1 | 8/2008 | Argyropoulos | |
| 2008/0190013 | A1 | 8/2008 | Argyropoulos | |
| 2008/0190321 | A1 | 8/2008 | Maase | |
| 2008/0213850 | A1* | 9/2008 | Shimoda et al. | 435/165 |
| 2008/0269477 | A1 | 10/2008 | Stegmann | |
| 2009/0020112 | A1 | 1/2009 | Massonne | |
| 2009/0044942 | A1 | 2/2009 | Gupta | |
| 2009/0062524 | A1 | 3/2009 | Massonne | |
| 2009/0088564 | A1 | 4/2009 | Luo | |
| 2009/0093027 | A1 | 4/2009 | Balan | |
| 2009/0143597 | A1* | 6/2009 | Dyson et al. | 548/109 |
| 2009/0176286 | A1 | 7/2009 | O'Connor | |
| 2009/0198046 | A1 | 8/2009 | Fanselow | |
| 2009/0203899 | A1 | 8/2009 | Buchanan | |
| 2009/0229599 | A1 | 9/2009 | Zhang | |
| 2009/0234146 | A1 | 9/2009 | Cooney | |
| 2009/0270248 | A1 | 10/2009 | Earl | |
| 2009/0326286 | A1 | 12/2009 | Yie et al. | |
| 2010/0055237 | A1* | 3/2010 | Zorn et al. | 426/18 |
| 2010/0151111 | A1* | 6/2010 | Nielsen et al. | 426/656 |

FOREIGN PATENT DOCUMENTS

| WO | WO 2005017252 A1 * | 2/2005 |
|---|---|---|
| WO | WO 2005/090563 | 9/2005 |
| WO | WO 2007111605 A1 * | 10/2007 |
| WO | WO 2008/043837 | 4/2008 |
| WO | WO 2008/090155 | 7/2008 |
| WO | WO 2008/090156 | 7/2008 |
| WO | WO 2008/095252 | 8/2008 |
| WO | WO 2009/018469 | 2/2009 |
| WO | WO 2009/024607 | 2/2009 |
| WO | WO 2009/030949 | 3/2009 |
| WO | WO 2009/030950 | 3/2009 |
| WO | WO 2009/105236 | 8/2009 |
| WO | WO 2009/124240 | 10/2009 |

OTHER PUBLICATIONS

Kilpelainen et al. J. Agric. Food Chem. (2007) 55: 9142-9148.*
English abstract for WO 2005090563 (Ohno et al.) downloaded from STN: file Caplus on Oct. 25, 2009.*
Tan et al. Green Chem. (2009) 11: 339-345.*
Dadi et al., "Enhancement of Cellulose Saccharification Kinetics Using an Ionic Liquid Pretreatment Step", Wiley InterScience, Biotechnology and Bioengineering, vol. 95, No. 5 (2006).
Dadi, "Mitigation of Cellulose Recalcitrance to Enzymatic Hydrolysis by Ionic Liquid Pretreatment", Applied Biochemistry and biotechnology, vol. 136-140, Humana Press, Inc. (2007).
Eggeman et al., "Process and Economic Analysis of Pretreatment Technologies", Bioresource Technology, vol. 96, pp. 2019-2025 (2005).
Fort, "Can Ionic Liquids Dissolve Wood? Processing and Analysis of Lignocellulosic Materials with 1-n-butyl-3-methylimidazolium chloride", The Royal Society of Chemistry, Green Chemistry, vol. 9, pp. 63-69 (2007).

(Continued)

*Primary Examiner* — Sandra Saucier
*Assistant Examiner* — Susan Hanley
(74) *Attorney, Agent, or Firm* — Hunton & Williams LLP

(57) ABSTRACT

A method for lignocellulose conversion to sugar with improvements in yield and rate of sugar production has been developed by using ionic liquid pretreatment. This new pretreatment strategy substantially improves the efficiency (in terms of yield and reaction rates) of saccharification of lignocellulosic biomass. Cellulose and hemicellulose, when hydrolyzed into their sugars, can be converted into ethanol fuel through well established fermentation technologies. These sugars also form the feedstocks for production of variety of chemicals and polymers. The complex structure of biomass requires proper pretreatment to enable efficient saccharification of cellulose and hemicellulose components to their constituent sugars. Current pretreatment approaches suffer from slow reaction rates of cellulose hydrolysis (by using the enzyme cellulase) and low yields.

30 Claims, 6 Drawing Sheets

OTHER PUBLICATIONS

Ghose, "Measurement of Cellulase Activities", International Union of Pure and Applied Chemistry, vol. 59, No. 2, pp. 257-268 (1987).

Kilpelainen et al., "Dissolution of Wood in Ionic Liquids", Journal of Agricultural and Food Chemistry, vol. 55, pp. 9142-9148 (2007).

Kim, "Pretreatment and Fractionation of Corn Stover by Ammonia Recycle Percolation Process", Bioresource Technology, vol. 96, pp. 2007-2013 (2005).

Kim and Holzapple, "Lime Pretreatment and Enzymatic Hydrolysis of Corn Stover", Bioresource Technology, vol. 96, pp. 1994-2006 (2005).

Lloyd and Wyman, Combined Sugar Yields for Dilute Sulfuric Acid Pretreatment Pretreatment of Corn Stover Followed by Enzymatic Hydrolysis of the Remaining Solids, Bioresource Technology, 96, pp. 1967-1977 (2005).

Miller, Miller, "Use of Dinitrosalicylic Acid Reagent for Determination of Reducing Sugar", Analytical Chemistry, vol. 31, No. 3, Mar. 1959.

Mosier et al., Optimization of pH Controlled Liquid Hot Water Pretreatment of Corn Stover, Bioresource Technology, 96, pp. 1986-1993 (2005).

Segal et al., "An Empirical Method for Estimating the Degree of Crystallinity of Native Cellulose Using the X-Ray Diffractometer", Textile Research Journal, pp. 786-794 (1959).

Swatloski et al., "Dissolution of Cellose with Ionic Liquids", Journal of American Chemical Society, vol. 124, pp. 4974-4975 (2002).

Teymouri et al., "Optimization of the Ammonia Fiber Explosion (AFEX) Treatment Parameters for Enzymatic Hydrolysis of Corn Stover", Bioresource Technology, vol. 96, pp. 2014-2018 (2005).

Wyman et al., "Coordinated Development of Leading Biomass Pretreatment Technologies", Bioresource Technology, 96, pp. 1959-1966 (2005).

Wyman, Comparative Sugar Recovery Data from Laboratory Scale Application of Leading Pretreatment Technologies to Corn Stover, Bioresource Technology, 96, pp. 2026-2032 (2005).

Zhang et al., 1-Allyl-3-Methylimidazolium Chloride Room Temperature Ionic Liquid: A New and Powerful Nonderivatizing Solvent for Cellulose, American Chemical Society, Macromolecules, vol. 38, pp. 8272-8277 (2005).

Zhang, "A Transition from Cellulose Swelling to Cellulose Dissolution by o-Phosphoric Acid: Evidence from Enzymatic Hydrolysis and Supramolecular Structure", Biomacromolecules, vol. 7, pp. 644-648 (2006).

Zhang et al, "Fractioning Recalcitrant Lignocellulose at modest Reaction Conditions", Biotechnology and Bioengineering, vol. 97, No. 2, pp. 214-223, Jun. 2007.

Non-Final Office Action mailed May 8, 2009 in U.S. Appl. No. 11/710,357, now U.S. Patent No. 7,674,608.

Co-Pending U.S. Appl. No. 12/687,049, filed Jan. 13, 2010, entitled "Saccharifying Cellulose".

International Search Report mailed Oct. 3, 2008 for International Patent Application No. PCT/US2008/03357.

* cited by examiner

BIOMASS PRETREATMENT

CROSS REFERENCE

This patent application is a conversion of and claims the benefit of provisional patent application 60/894,708, filed Mar. 14, 2007.

TECHNICAL FIELD

This invention relates to the conversion of lignocellulosic biomass to sugar. More specifically, the lignocellulosic biomass first is pretreated with an ionic liquid.

BACKGROUND OF THE INVENTION

In lignocellulosic biomass, crystalline cellulose fibrils are embedded in a less well-organized hemicellulose matrix which, in turn, is surrounded by an outer lignin seal. Contacting naturally occurring cellulosic materials with hydrolyzing enzymes generally results in cellulose hydrolysis yields that are less than 20% of theoretically predicted results. Hence, some "pretreatment" of the biomass is invariably carried out prior to attempting the enzymatic hydrolysis of the polysaccharides (cellulose and hemicellulose) in the biomass. Pretreatment refers to a process that converts lignocellulosic biomass from its native form, in which it is recalcitrant to cellulase enzyme systems, into a form for which cellulose hydrolysis is effective. Compared to untreated biomass, effectively pretreated lignocellulosic materials are characterized by an increased surface area (porosity) accessible to cellulase enzymes, and solubilization or redistribution of lignin. Increased porosity results mainly from a combination of disruption of cellulose crystallinity, hemicellulose disruption/solubilization, and lignin redistribution and/or solubilization. The relative effectiveness in accomplishing some (or all) of these factors differs greatly among different existing pretreatment processes. These include dilute acid, steam explosion, hydrothermal processes, "organosolv" processes involving organic solvents in an aqueous medium, ammonia fiber explosion (AFEX), strong alkali processes using a base such as, ammonia, NaOH or lime, and highly-concentrated phosphoric acid treatment. Many of these methods do not disrupt cellulose crystallinity, an attribute vital to achieving rapid cellulose digestibility. Also, some of these methods are not amenable for "easy recovery" of the chemicals employed in the pretreatment.

Of the existing pretreatment technologies, a coordinated development of the leading ones was recently reported (C. E. Wyman et al, *Bioresource Technology*, (2005) 96, 1959). A consortium of researchers (Biomass Refining Consortium for Applied Fundamental and Innovation (CAFI)) have studied the pretreatment of a well-characterized single feed stock, namely corn stover, by several then promising pretreatment technologies using common analytical methods, and a consistent approach to data interpretation (C. E. Wyman et al., *Bioresource Technology*, (2005) 96, 2026). In particular, the following were investigated: (1) dilute acid hydrolysis (T. A. Lloyd and C. E Wyman, *Bioresource Technology*, (2005) 96, 1967), (2) Ammonia Fiber Explosion (AFEX) technique (F. Teymouri et al., *Bioresource Technology*, (2005) 96, 2014), (3) pH Controlled liquid hot water treatment (N. Mosier et al., *Bioresource Technology*, (2005) 96, 1986), (4) aqueous ammonia recycle process (ARP) (T. H. Kim and Y. Y. Lee, *Bioresource Technology*, (2005) 96, 2007), and (5) lime pretreatment (S. Kim and M. T. Holzapple, *Bioresource Technology*, 96, (2005) 1994) were investigated. All of the above-mentioned methods have two steps: a pretreatment step that leads to a wash stream, and an enzymatic hydrolysis step of pretreated-biomass that produces a hydrolyzate stream (FIG. 2). The combined total amounts of five and six carbon sugars and their oligomers in both these effluent streams were used to estimate the overall sugar yields in each of these methods.

In the above methods, the pH at which the pretreatment step is carried out increases progressively from dilute acid hydrolysis to hot water pretreatment to alkaline reagent based methods (AFEX, ARP, and lime pretreatments). Dilute acid and hot water treatment methods solubilize mostly hemicellulose, whereas methods employing alkaline reagents remove most lignin during the pretreatment step. As a result, the wash stream from the pretreatment step in the former methods contains mostly hemicellulose-based sugars, whereas this stream has mostly lignin for the high-pH methods. The subsequent enzymatic hydrolysis of the residual biomass leads to mixed sugars (C5 and C6) in the alkali based pretreatment methods, while glucose is the major product in the hydrolyzate from the low and neutral pH methods. The enzymatic digestibility of the residual biomass is somewhat better for the high-pH methods due to the removal of lignin that can interfere with the accessibility of cellulase enzyme to cellulose. All these methods are carried out in aqueous media at temperatures well above the normal boiling point of water to facilitate the physico-chemical phenomena involved in the depolymerization/melting of hemicellulose and lignin and require a high pressure environment (6 to 20 atm). Also, none of these methods can effectively disrupt the crystallinity of cellulose in the biomass. Furthermore, some of these methods release most of the xylose in the form of xylooligosaccharides, which are not easily fermented by many microorganisms and require additional steps to break them into monomeric species. Finally, a comparative economic analysis of these leading pretreatment technologies (T. Eggeman and R. T. Elander, *Bioresource Technology*, (2005) 96, 2019) indicates that they are all capital intensive compared to corn dry mill and significant process improvements are necessary for commercialization.

Organosolv methods in which solvents such as ethanol and methanol are used (in aqueous media) and methods using bases such as NaOH are also suggested in the literature. These methods are also capable of dissolving lignin, but they are not able to disrupt the crystallinity of cellulose. Further, the costs are so high that these methods are not considered competitive for manufacture of high-volume, low-value commodity products. Based on the information available on the concentrated phosphoric acid method (Zhang, Y-H P et al, Biotechnol. Bioeng. 97:214-223), it appears to be an elaborate method involving several steps making the overall process expensive. However, due to the harsh conditions used, amorphous cellulose is obtained by this pretreatment process.

Dissolution and processing of pure cellulose using ionic liquids was reported earlier (Swatloski, R. P., Rogers, R. D., Holbrey, J. D., U.S. Pat. No. 6,824,599, 2002; Holbrey, J. D., Spear, S. K., Turner, M. B., Swatloski, R. P., Rogers, R. D., U.S. Pat. No. 6,808,557, 2003). In a recent work, we reported on an effective approach to mitigate the recalcitrance of cellulose to enzymatic hydrolysis by Ionic liquid pretreatment (Dadi, A., Schall, C. A., Varanasi, S., " ", Applied Biochemistry and Biotechnology, vol. 136-140, p 407, 2007; Varanasi, S., Schall, C., and Dadi, A., US patent filed: February 2007). While this approach makes use of an ionic liquid to open the structure of pure crystalline cellulose material such as Avicel to make it accessible to cellulase enzymes, it did not specifically address the pretreatment of lignocellulosic biomass, which is the subject of this invention. In this context, it is noted that very recently isolation of cellulose from biomass by using ionic liquids (Fort, D. A., Remsing, R. C., Swatloski, R. P., Moyna, P., Moyna, G., Rogers, R. D., *Green Chemistry* 9: 63-69, 2007) and complete dissolution of biomass in ionic liquids (Vesa, M. Aksela, R., European Patent WO2005017001, 2005) have been investigated. The former application focuses on "in tact recovery" of cellulose portion of the biomass for materials development, whereas the latter aims to identify ILs and conditions that will lead to a "total dissolution" of biomass. However, currently a high yield pretreatment approach that can be used to rapidly and efficiently saccharify the polysaccharide portions of lignocellulosic biomass is unavailable. This invention exploits the differing "affinities" of the three major components of biomass (i.e., lignin, hemicellulose and cellulose) towards ILs, coupled with the unique capability of some ILs in disrupting the crystallinity of the cellulose portion (by breaking the hydrogen-bonding structure), to devise a scheme to efficiently saccharify the polysaccharide portions of biomass. The invention requires neither the extraction of cellulose from biomass nor the dissolution of biomass in IL.

SUMMARY OF THE INVENTION

Lignocellulosic biomass is an attractive feed-stock because it is an abundant, domestic, renewable source that can be converted to liquid transportation fuels, chemicals and polymers. The major constituents of lignocellulose are the following: (1) hemicellulose (20-30%), an amorphous polymer of five and six carbon sugars; (2) lignin (5-30%), a highly cross-linked polymer of phenolic compounds; and (3) cellulose (30-40%), a highly crystalline polymer of cellobiose (a glucose dimer). Cellulose and hemicellulose, when hydrolyzed into their sugars, can be converted into ethanol fuel through well established fermentation technologies. These sugars also form the feedstocks for production of a variety of chemicals and polymers. The complex structure of biomass requires proper pretreatment to enable efficient saccharification of cellulose and hemicellulose components into their constituent sugars. Current pretreatment approaches suffer from slow reaction rates of cellulose hydrolysis (using the enzyme cellulase) and low sugar yields (C. E. Wyman et al., 2005, Bioresource Technology: 96, 1959).

A method for conversion of the carbohydrates of lignocellulose to sugars with improvements in yield and rate of sugar production has been developed by using ionic liquid (IL) pretreatment. This new pretreatment strategy substantially improves the efficiency (in terms of yield and reaction rates) of saccharification of lignocellulosic biomass. Other unique features of this IL-pretreatment method that have a major impact on the overall economics of sugar production from biomass (and are in stark contrast to most leading methods) are its (i) ability to process a variety of lignocellulosic biomass sources with ILs capable of disrupting native cellulose structure (ii) ability to handle large biomass to IL ratios during incubation (iii) ability to accomplish saccharification at very low enzyme loadings (iv) ability to perform well with large biomass particles (v) potential for total recovery (through facile means) and multiple reuse of the IL employed to pretreat the biomass, (vi) ability to produce a hydrolysate free of compounds that can inhibit the down-stream processing of the constituent sugars, (as exemplified by ethanol and lactic acid production), and (vii) Allows for recovering most of the lignin in biomass following saccharification.

DETAILED DESCRIPTION OF THE INVENTION

The present invention is a new strategy for the pretreatment of lignocellulosic biomass by using Ionic Liquids (ILs) to facilitate efficient and rapid enzymatic hydrolysis of its carbohydrates.

Figure 1:
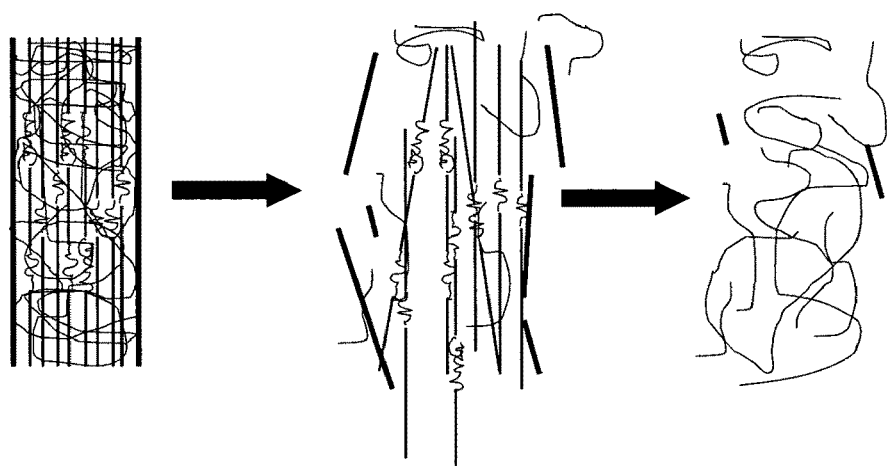
FIG. 1 is a schematic representation of biomass prior to and following pretreatment process of this invention. Lignin, hemicellulose and cellulose are represented in the figure. In untreated biomass, highly-crystalline cellulose fibrils are embedded in a less well-organized hemicellulose matrix which, in turn, is enveloped by lignin cladding—left-most cartoon in the figure. An ideal pretreatment of biomass should enable the following tasks: (i) displace/remove the lignin cladding, (ii) open-up/remove the hemicellulose, and (iii) reduce/eliminate the crystallinity of the cellulose fraction. The figure depicts these three tasks in two steps: step 1 includes tasks (i) and (ii), and step 2 represents task (iii). Most existing pretreatment methods only accomplish tasks (i) and (ii), (i.e. step 1), but not step 2. However, step 2 is critically important in reducing the time and enzyme loading necessary for accomplishing the hydrolysis efficiently.

Lignocellululosic biomass including agricultural (e.g., corn stover) and forestry residues (e.g. sawdust) and herbaceous (e.g., switch grass) and wood (e.g. poplar trees) crops are sufficiently abundant to provide a major resource for making fuels and chemicals. In lignocellulosic biomass, crystalline cellulose fibrils are embedded in a less well-organized hemicellulose matrix which, in turn, is surrounded by an outer lignin seal. Chemical/Biochemical hydrolysis of the polysaccharides, cellulose and hemi-cellulose, into their monomeric sugars provides the basic precursors useful for producing fuels and chemicals from biomass (the so called "sugar platform"). However, cellulosic biomass must be pretreated to realize high yield of sugars during hydrolysis. FIG. 1 is a schematic representation of biomass prior to and following pretreatment.

Figure 2:
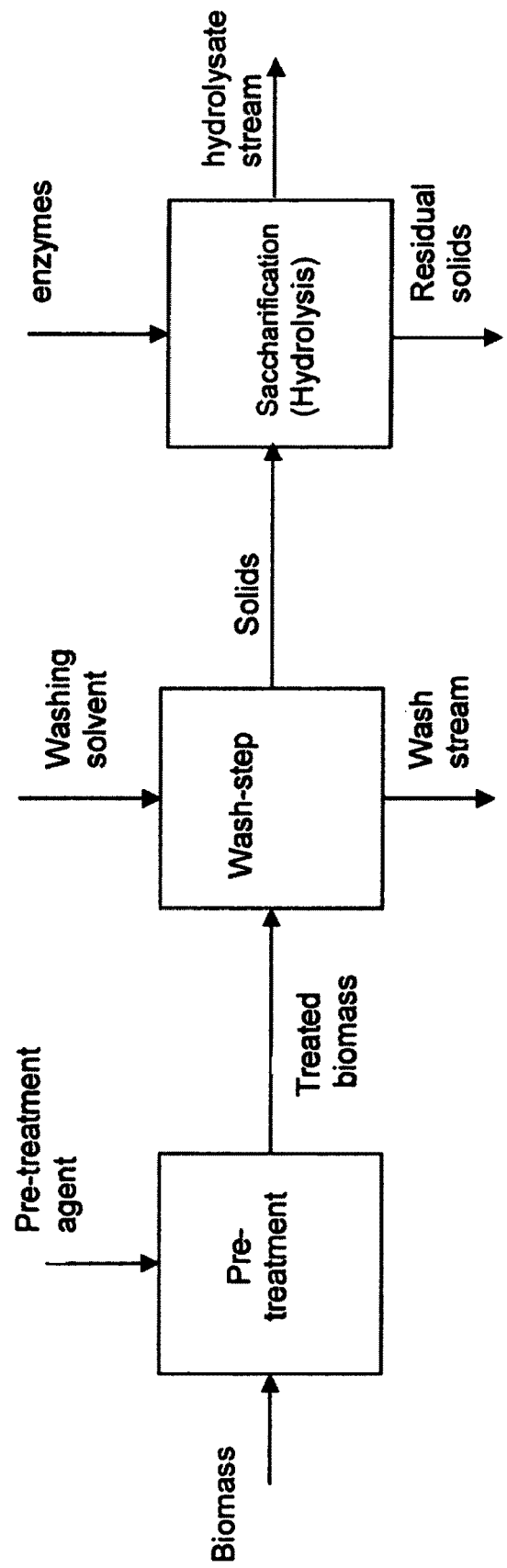
FIG. 2. A process schematic of the "sugar-platform" for producing fuels and chemicals from lignocellulosic biomass.

FIG. 2 is a schematic of a typical process for producing sugars from biomass. Pretreatment, which is among the most costly steps, has a major influence on the cost of both prior (e.g., size reduction) and subsequent (e.g. enzymatic hydrolysis) operations in sugar production.

Ionic liquids have extremely low volatility and when used as solvents, they do not contribute to emission of volatile components. In this sense they are environmentally benign solvents. ILs have been designed to dissolve cellulose and lignocellulose. Following dissolution, cellulose can be regenerated by the use of anti-solvents. However, the complete dissolution of lignocellulosic materials (particularly woods) in ILs is harder and, even partial dissolution, requires very long incubation of biomass in IL at elevated temperatures. Even then, a high yield of cellulose is not generally achieved after regeneration (Fort, D. A. et al., 2007, *Green. Chem.*: 9, 63).

Figure 5:
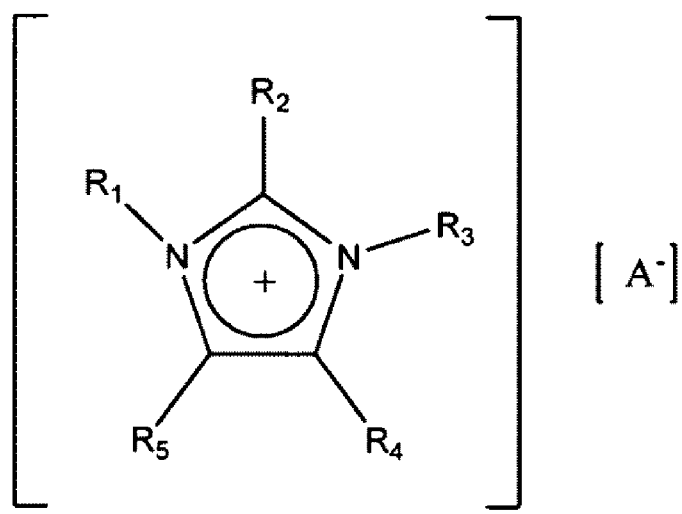
FIG. 5. A generic imidazolium based ionic liquid structure.
Figure 6:
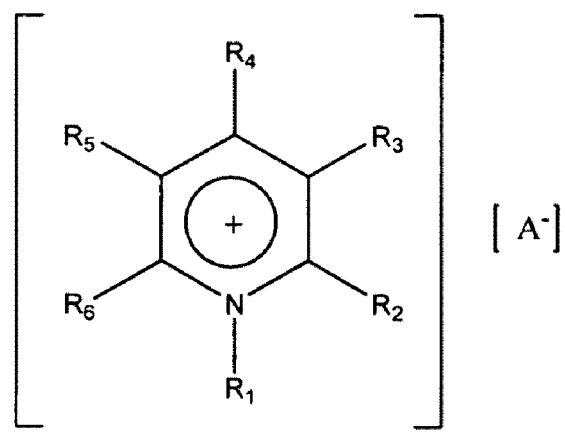
FIG. 6. A generic pyrridinium based ionic liquid structure.

Our invention differs from the above-mentioned classic approach to the use of ionic liquids in that we do not aim to dissolve lignocellulose, but rather to contact it with the IL for very short times sufficient to mainly disrupt lignin sheathing and swell the remaining biomass structure significantly (at least 30%). This pretreatment enables the subsequent enzymatic hydrolysis process to proceed in a relatively short period of time as well as give quantitative yields of glucose and high yields of pentose sugars. Any ionic liquid capable of disrupting the hydrogen bonding structure to reduce the crystallinity of cellulose in the biomass can be used in the pretreatment strategy outlined here represented by a cation structure that includes imidazolium, pyrroldinium, pyridinium, phosphonium, or ammonium and all functionalized analogs thereof. For example, the structure as shown in FIG. 5 wherein each of R1, R2, R3, R4, and R5 is hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein A is a halide, hydroxide, formate, acetate, propionate, butyrate, any functionalized mono- or di-carboxylic acid having up to a total of 10 carbon atoms, succinate, lactate, aspartate, oxalate, trichloroacetate, trifluoroacetate, dicyanamide, or carboxylate. Another example of the structure of IL is shown in FIG. 6 wherein each of R1, R2, R3, R4, R5, and R6 is hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein A is a halide, hydroxide, formate, acetate, propanoate, butyrate, any functionalized mono- or di-carboxylic acid having up to a total of 10 carbon atoms, succinate, lactate, aspartate, oxalate, trichloroacetate, trifluoroacetate, dicyanamide, or carboxylate. The halide can be a chloride, fluoride, bromide or iodide.

Also an ionic liquid mixture with a composition described by Equation 1 can be used.

$$\sum_{n=1}^{20} [C^+]_n [A^-]_n \quad (1)$$

$C^+$ denotes the cation of the IL and $A^-$ denotes the anionic component of the IL In Equation 1. Each additional IL added to the mixture may have either the same cation as a previous component or the same anion as a previous component, of differ from the first only in the unique combination of the cation and anion. For example, consider below the five component mixture of ILs in which common cations and anions are used, but each individual IL component is different:
$[BMIM^+][Cl^-]+[BMIM^+][PF_6^-]+[EMIM^+][Cl^-]+[EMIM^+][PF_6^-]+[EMIM^+][BF_4^-]$
The final mixture of ionic liquids will vary in the absolute composition as can be defined by the mole percent of various functionalized cations and anions. Therefore, the mixture shall be comprised of varying weight percentages of each utilized component, as defined by Equation 1.

We demonstrate the use of several such representative solvents for pretreating biomass in this invention including a "new IL", 1-Ethyl-3-Methylimidazolium Propionate (EMIM-Pr) synthesized by us. (see, Example IV).

Figure 3:
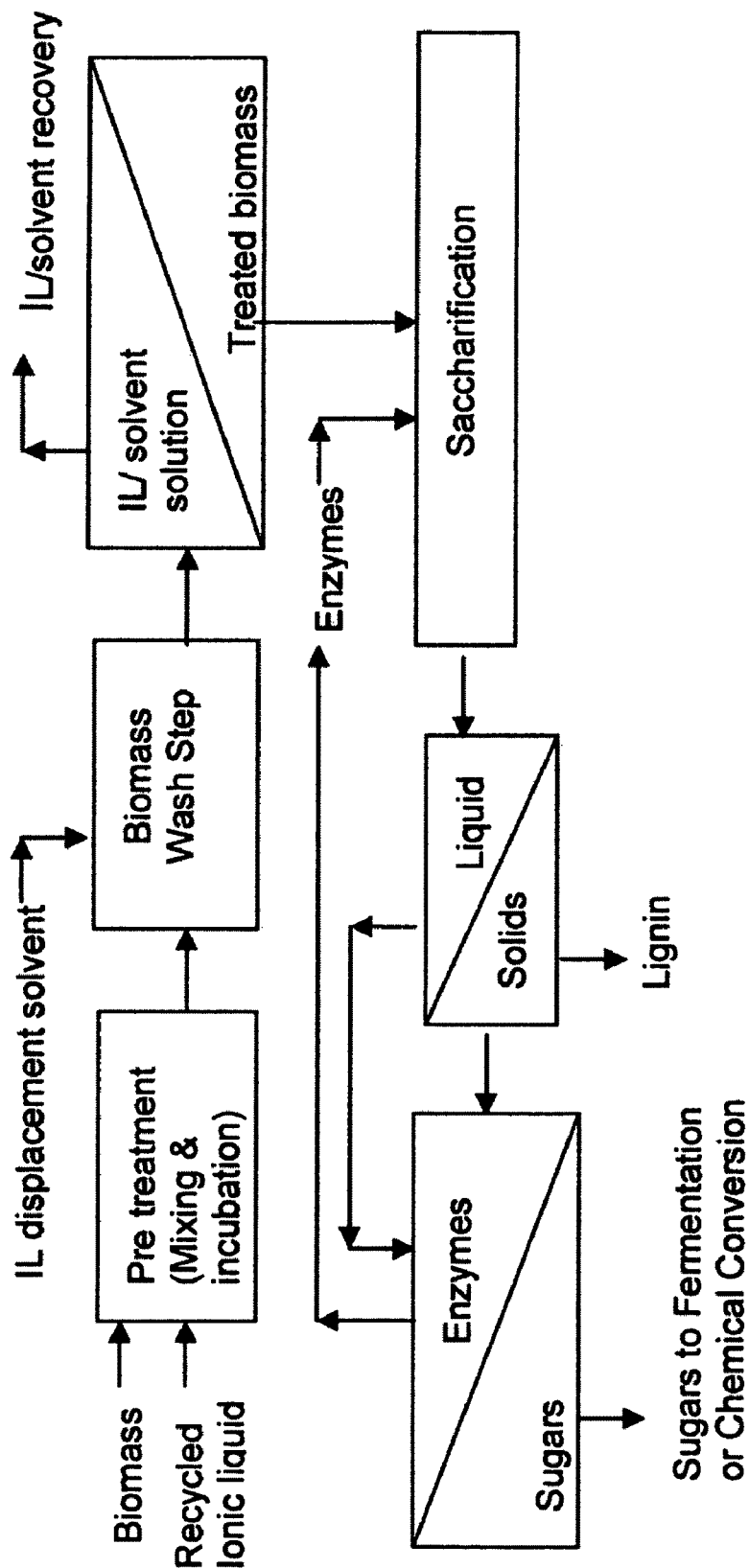
FIG. 3. Major processing steps for the ionic liquid pretreatment of biomass. Biomass is pretreated by incubation with an ionic liquid, followed by IL extraction with a wash solvent such as alcohol or water. The treated biomass can then be separated from the ionic liquid/wash-solvent solution by centrifugation or filtration, and sent to the hydrolysis (saccharification) reactor. The wash solvent (i.e. Methanol, ethanol or water) can be separated from the non-volatile ionic liquid in a flash distillation step with ionic liquid recycled back to the pretreatment tank and solvent recycled back to the biomass wash step. Enzymes can be recovered from the saccharification reactor and recycled. The residual solids portion following saccharification is mostly lignin which can be recovered for further processing.

The goal of the IL pretreatment process is not achieving any dissolution of lignocellulose, but contacting it with the IL for sufficient time to redistribute lignin and swell the remaining biomass structure (depicted in FIG. 4) to enhance the hydrolysis rate and conversion of cellulose and hemicellulose to their constituent sugars. Following saccharification with an appropriate enzyme mix, capable of converting all the carbohydrates in the pre-treated biomass to sugars, most of the solids left behind in the saccharification reactor represent the lignin portion of the biomass. This provides a method of recovering the lignin from biomass. Also, ultra-filtration of the liquid portion of the hydrolysate, provides a means of recovering the hydrolysis enzymes for reuse from the sugar solution which is the precursor for the production of a number of fuels and chemicals (FIG. 3).

Corn stover (an agricultural residue) and poplar (hard wood) were used as representative lignocellulosic materials in the pretreatment examples outlined. The compositional analyses of the corn stover and poplar feedstocks used in all experiments are given in Table 1a and Table 1b. Glucose is the only sugar that is generated from cellulose, whereas all other hexose and pentose sugars are derived from hemicellulose.

TABLE 1a

USDA Corn Stover compositional analysis by LAPS analysis

| Component | Weight % (dry weight basis) |
|---|---|
| Glucan | 34 |
| Xylan | 20 |
| Arabinan | 2.9 |
| Mannan | 1.4 |
| Galactan | 1 |
| Lignin | 18.8 |
| Ash | 7 |

TABLE 1b

Poplar compositional analysis by LAPS analysis

| Component | Weight % (dry weight basis) |
|---|---|
| Glucan | 43.1 |
| Xylan | 14 |
| Arabinan | 4 |
| Mannan | 1.8 |
| Galactan | 1.7 |
| Lignin | 29 |
| Ash | 0.8 |

One of the following representative ionic liquids 1-n-butyl-3-methylimidazolium chloride (BMIMCl)/1-n-ethyl-3-methyl imidazolium acetate (EMIMAc)/1-ethyl-3-methyl imidazolium propionate (EMIMPr)/1-allyl-3-methyl imidazolium chloride/3-methyl-N-butylpyridinium chloride was contacted with small particles of dry corn stover or poplar (−20+80 mesh sized particles) for varying times (~5 minutes to 8 hours) hour at ~50° C. to 200° C. Incubation with biomass can be carried out using conventional heating or microwave irradiation as long as the ionic liquid is in molten state during incubation. The IL-incubated biomass was then contacted with one of the representative wash-solvents, namely, methanol/ethanol/water/acetonitrile/butanol/propanol. The wash-solvent mixes with the IL (in all proportions) and hence is able to extract it from the incubated biomass. The treated biomass can then be separated from the ionic liquid/wash solvent solution by centrifugation. The biomass, stripped off the IL, was then hydrolyzed with a commercial cellulase system The IL can be recovered from the wash-solvent and any dissolved biomass components from the wash-step through suitable separation methods including one or more of the following:

activated charcoal treatment, distillation, membrane separation, electrochemical separation techniques, solid phase extraction, and liquid-liquid extraction. The ionic liquid can then be recycled back to the pretreatment tank. The wash solvent also can be recycled back for reuse in washing IL-incubated biomass. With high conversion of polysaccharides to their monomeric sugars, enzymes can potentially be recovered from the saccharification reactor and recycled. Complete removal of wash solvent (water) is not necessary before the IL is recycled (see Example VII). Many other pretreatment methods are not amenable to easy recovery of the chemicals employed in the process. FIG. 3 is a process schematic of this pretreatment process.

Examples I through IV below and the associated Tables 2 through 8 illustrate representative results of our IL-pretreatment method. In pretreatment of biomass (corn stover and poplar) with IL, ~90% conversion of glucan (cellulose) to glucose was achieved in about 16 hours in addition to high conversion (~50 to 70%) of xylan (from hemi-cellulose) to xylose by using only cellulases supplemented with cellobiase to saccharify both polysaccharides. Glucan (cellulose) conversion to glucose increases monotonically with an increase in temperature. Xylan (hemicellulose) conversion to xylose generally increases with increasing IL temperature, but can decrease at very high temperatures. Optimization of pretreatment conditions is shown to yield high conversions of both glucan and xylan to their monomeric sugars in the saccharification step.

Untreated corn stover biomass only yields 27% glucan conversion in 36 hrs, while most of the established pretreatment methods take from 72 to 170 hours to complete the hydrolysis. More details on the specifics of corn stover and poplar pretreatment by using BMIMCl/EMIMAc/EMIMPr are provided in the examples.

For other pretreatment methods, included in the CAFI study [Wyman, C. E., et al., *Bioresource Tech.*, 2005. 96: p. 2026-2032], conversion of glucan (cellulose) to glucose and xylan (hemicellulose) to xylose can be calculated from the reported yields after 72 hours of hydrolysis (FIG. 2, step 2) at enzyme loadings of 15 FPU/g glucan (same loading used in our saccharification data). Conversion of glucan to glucose varied from 85 to 96%. Conversion of xylan to xylose varied from 5 to 91%. This conversion to xylose occurred almost exclusively during the pretreatment step (FIG. 2, wash stream) except in the case of AFEX. In AFEX, xylan conversion occurred in the hydrolysis step with 78% conversion to xylose and 91% conversion to xylose plus soluble xylose oligomers. High conversion of glucan to glucose was achieved in less than 24 hours with our IL pretreatment and compares favorably with the alternative pretreatment technologies reported by CAFI. Xylose conversions with IL pretreatment also compared favorable with the results reported by CAFI. Many alternative pretreatments (with the exception of AFEX), result in xylan hydrolysis before enzyme addition. It appears from our results that little xylan hydrolysis or hemicellulose derivatization occurs during IL pretreatment. The xylan is then available for enzyme catalyzed hydrolysis by the cellulase mixture used in our preliminary studies. Using additional xylanases and arabinases in our enzyme mixture has the potential to further improve the xylose yields.

Further, unlike most water-based pretreatment methods, IL-pretreatment does not produce sugars or their degradation products during incubation step because these are generally hydrolysis products that require presence of water. Sugars are produced only upon enzyme addition. The absence of sugar degradation products that can prove inhibitory to the subsequent processing of the sugars (such as fermentation to alcohol and lactic acid) eliminates the need for the additional step of "conditioning"—in which these inhibitory products are removed—of the hydrolysate. (see examples XI and XII).

A more direct comparison of 24 hour hydrolysis can be made with that reported for the AFEX pretreatment process for corn stover. With 15 FPU/g glucan cellulase enzyme loadings, glucan conversion was about 62% and xylan conversion was about 45% for the AFEX process [Teymouri, F., et al., *Bioresource Tech.*, 2005. 96(18): p. 2014-2018]. With IL pretreatment at the same cellulase loadings, 24 hour conversion of corn stover glucan exceeded 80% and xylan conversion was ~45%. Poplar conversion of glucan exceeded 90% and xylan conversion to monomeric sugars exceeded 65% with IL pretreatment.

Majority of the pretreatment methods proposed in literature, with the exception of phosphoric acid treatment [Zhang, Y.-H. P., et al., Biomacromolecules, 2006. 7(2): p. 644-648], do not disrupt cellulose crystallinity, an attribute vital to achieving rapid cellulose digestibility (hydrolysis). A measure of biomass crystallinity can be obtained through interpretation of X-ray powder diffraction (XRD) data. Crystallinity of poplar after IL pretreatment was measured using XRD and crystallinity index, CrI, was calculated using a standard technique developed for cellulose [Segal, L., et al., *Text Res. J.*, 1959. 29: p. 786-94]. Native poplar has a measured CrI between 40 to 50. A CrI of about 10 is indicative of almost complete decrystallization of the cellulose portion. As seen in Table 18, there is a strong correlation between saccharification kinetics and CrI. This data explains why the IL-pretreatment is able to achieve saccharification at a significantly rapid rate compared to most other pretreatment methods.

These observed rapid hydrolysis rates with IL-pretreatment also open up the possibility of accomplishing the saccharification using much "lower enzyme loadings" compared to those traditionally used with most other pretreatment methods. Indeed, as shown in Example V we were able to cut down the enzyme loadings to ⅔ or ⅓ of what has bee used in most CAFI studies (i.e. 15 FPU of cellulase and 60 CBU of β-glucosidase per g of glucan), and yet achieve equivalent glucose and xylose yields (see Table 9). This is a very important result, as the cost of enzymes contributes significantly to the overall cost of producing sugars from biomass.

Figure 4:
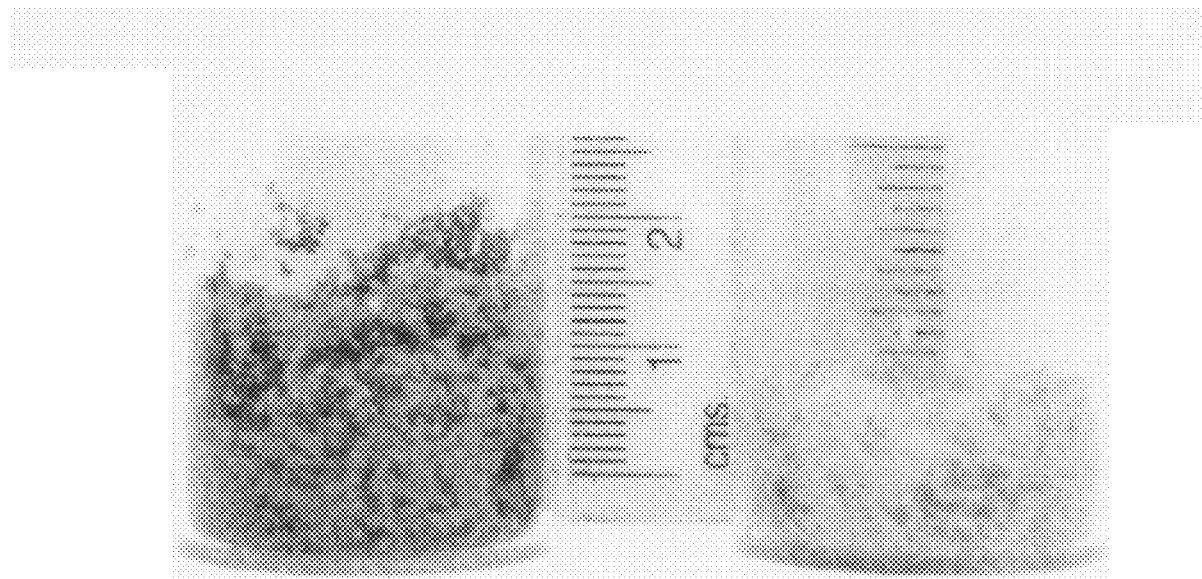
FIG. 4: The vial on the left contains 33 weight % poplar in a poplar/IL blend after incubation at 120° C. for one hour. The vial on the right contains untreated poplar and IL (in its solid state) at room temperature. Significant swelling (~100%) observed with IL-treated poplar following incubation at this weight fraction.

Since IL-pretreatment needs only just enough IL to swell the biomass structure, we are able to process very large quantities of biomass with minimal IL usage during the incubation step. This is illustrated in Example III, wherein weight ratios of poplar to IL as high as 1:2 were used in the incubation step. At these high poplar loadings, the incubated mixture basically is a wet swollen powder as shown in FIG. 4. This wet powder, upon enzyme hydrolysis after washing off IL, yields very high glucose and xylose conversions as can be seen from Table 6.

Not only were we able to significantly lower the usage of the pretreatment solvent (i.e. the IL), but also were able to recover it completely (~100%) by washing the incubated biomass with a wash solvent several times, as shown in Example VIII (Tables 13 through 17). This example proves that IL does not irreversibly adsorb on any of the biomass components, even at high biomass/IL ratios, where the available surface area of the biomass is very high.

We recovered the IL from the IL/wash solvent mixtures by evaporation of the wash solvent (ethanol and/or water) from the extremely low volatility IL. The recovered IL was then used with no additional cleaning steps in subsequent biomass pretreatment cycles at constant pretreatment conditions. We have repeatedly used the recycled IL and did not notice any loss of its effectiveness in pretreating the biomass, even after 15 cycles as shown in Example IX (see, Tables 19, 20, and 21). This ability to repeatedly reuse the IL with minimal cleaning will have a profound effect on the economics of IL-pretreatment.

Residual water in the recycled IL can lower the IL's capacity to sever the inter- and intra-chain hydrogen bonds imparting crystallinity to cellulose. In order to affect swelling of biomass, several of the cellulosic hydrogen-bonds have to be disrupted. Accordingly, we expect dissolved water to affect IL's performance as a biomass pretreatment solvent. The admissible water content in IL can affect the economics of the pretreatment method in two aspects. First, it determines how dry the IL has to be before it can be reused. Second, it determines how dry the biomass has to be during incubation with IL. In Example VII we studied the effect of water content of IL on its effectiveness, and observed that the effectiveness of the IL is not compromised to any appreciable extent until the dissolved water content exceeds about 15% by weight. (See Table 12).

Pretreatment methods that work efficiently with large biomass particles are of particular value because the energy requirements (and hence the costs) associated with preprocessing (size-reduction) of the feedstock decrease exponentially as the acceptable "average particle size" for pretreatment increases. Accordingly, in Example VI we studied the effect of biomass particle size on the saccharification rates and yield of sugars in our pretreatment technology. We show that our pretreatment technique works equally well with particles ranging in size from 850 µm to 180 µm (see, Table 10).

Our IL-pretreatment-and-saccharification technique allows for recovering the lignin in the biomass in the form a post saccharification solid residue (Example X).

Finally, the sugars in the hydrolysate obtained following IL-pretreatment of poplar can be converted to fuel ethanol (Example XI) or other bioproducts such as lactic acid (Example XII) with no further conditioning and adverse effects from any residual traces of IL in the hydrolysate. Further chemical/biochemical processing of this residue will lead to compounds which could be used for the production of fuels, chemicals, polymers and other materials.

Example I

Corn Stover Pretreated with BMIMCl for Varying Temperature/Times

The incubation time and temperature were systematically varied to achieve optimal glucan and xylan conversions to their monomeric sugars. Corn stover was incubated for 10 minutes, 1 or 3 hours and at 130 or 150° C. in BMIMCl.

Pretreatment: Corn stover was mixed with IL to form a 5 weight percent biomass in the mixture (5% w/w). The mixture was incubated with mixing at 130 or 150° C. for 10 minutes, 1 hour and 3 hours. The ionic liquid was extracted from the biomass by addition of water, centrifuged and the supernatant was removed. The solid residue was washed until IL was completely extracted.

Enzymatic hydrolysis: The washed solid was added to a reaction buffer (0.05 M Na citrate buffer, pH 4.8) to form a one percent by weight mixture of biomass solids in the buffer. A commercial cellulase, SPEZYME CP, was used at a concentration of 20 FPU/g corn stover (60 FPU/g glucan) where FPU represents filter paper units. β-glucosidase was supplemented by addition of 40 CBU/g corn stover (120 CBU/g glucan) of NOVOZYME 188 where CBU represents cellobiase units. Percent conversion to glucose and xylose is based on the mass of corn added in the pre-treatment step and the glucan and xylan content of the corn stover. (Table 1a). Sugar concentration was analyzed by using high performance liquid chromatography with refractive index detection.

Results: The conversion of corn stover glucan and xylan to glucose and xylose, respectively, as a function of time during enzyme hydrolysis is shown in Tables 2 and 3. Pretreatment with IL resulted in significant increases in the rate of hydrolysis of glucan to glucose compared to the untreated corn stover samples (Table 2). Conversion of xylan to xylose also increased with IL pretreatment when compared to untreated corn stover (Table 3) Biomass pretreated at 150° C. for 1 hr, upon saccharification (enzyme hydrolysis), yielded 100% conversion of cellulose to glucose and 61% conversion of xylan to xylose within 36 hours of hydrolysis. This result is significant because most existing pretreatment methods require 72 to 170 hrs of hydrolysis to realize cellulose conversions greater than 90%.

Incubating the biomass in IL for longer than 1 hr at 150° C. does not appear to improve xylose yields, although 100% glucose yields are still realized. In fact, incubating at 150° C. for 3 hrs seems to lower the xylose yield compared to incubation at 150° C. for 1 hr (Table 3).

TABLE 2

Percent corn stover glucan conversion to glucose with varying incubation time and temperature as a function of hydrolysis (Hyd) time.

| Hyd Time (hr) | Conversion to glucose (%) Incubation Temperature (° C.) and Time in hr | | | | | | |
|---|---|---|---|---|---|---|---|
| | Untreated | 130° C. 10 min | 130° C. 1 hr | 130° C. 3 hr | 150° C. 10 min | 150° C. 1 hr | 150° C. 3 hr |
| 6 | 14 | 41 | 31 | 44 | 42 | 61 | 75 |
| 28 | 27 | 48** | 58 | 65 | 52** | 85 | 91 |
| 36 | 26 | — | 68 | 70 | — | 100 | 100 |

**Glucose conversion at 24 hours hydrolysis.

TABLE 3

Percent corn stover xylan conversion to xylose with varying incubation time and temperature as a function of hydrolysis time.

| Hydrolysis Time (hr) | Conversion to xylose (%) Incubation Temperature (° C.) and Time in hr | | | | |
|---|---|---|---|---|---|
| | Untreated | 130, 1 hr | 130, 3 hr | 150, 1 hr | 150, 3 hr |
| 14 | 1 | 18 | 29 | 39 | 12 |
| 36 | 3 | 36 | 40 | 61 | 22 |

Example II

Corn Stover and Poplar with EMIM Acetate

1-Ethyl-3-Methylimidazolium acetate (EMIM Acetate), in addition to having a high capacity to disrupt the hydrogen bonding structure of crystalline cellulose, is a liquid at room temperature and has a lower melting point than BMIMCl. These traits make it a more convenient representative IL from a process standpoint compared to BMIMCl. This example describes the pretreatment experiments with EMIM acetate.

Corn stover and poplar, were ground and separated to the same sieve cut, The samples were mixed with EMIMAc to form a biomass/IL mixture of 5 weight % biomass and incubated with mixing at varying temperatures and times, followed by washing with water.

Enzyme hydrolysis: The procedure for the enzyme hydrolysis is the same as that outlined in Example I (1 weight % biomass in saccharification buffer) except for changes in enzyme loading noted below. The percent conversion to glucose and xylose reported was based on the quantity of biomass (corn stover/popolar) added in the pre-treatment step and the sugars content of this quantity. The samples were hydrolyzed at a fixed enzyme loading of 15 FPU/g glucan of cellulase (SPEZYME CP) and 60 CBU/g glucan of β-glucosidase (NOVOZYME 188).

Results: As seen in Tables 4 and 5, glucan (cellulose) conversion to glucose increases monotonically with an increase in temperature. Xylan (hemicellulose) conversion to xylose generally increases with increasing IL temperature but can decrease at high pretreatment temperature.

TABLE 4

Conversion of glucan and xylan to glucose and xylose after 10 and 24 hours of enzyme hydrolysis is given for poplar incubated in EMIMAc at varying pretreatment temperatures and times (first column). The weight fraction of biomass in the IL-biomass mixture was 5%.

| Temp/Time | 10 hr Conv. | | 24 hr Conv. | |
|---|---|---|---|---|
| (° C.\|h) | Glucan | Xylan | Glucan | Xylan |
| 120\|0.5 | 89 | 62 | 97 | 70 |
| 100\|1 | 75 | 57 | 86 | 65 |
| 75\|1 | 62 | 37 | 75 | 47 |

TABLE 5

Conversion of glucan and xylan to glucose and xylose after 10 and 24 hours of enzyme hydrolysis is given for corn stover incubated in EMIMAc at varying pretreatment temperatures and times. The weight fraction of biomass in the IL-biomass mixture was 5%.

| Temp/Time | 10 hr Conv. | | 24 hr Conv. | |
|---|---|---|---|---|
| (° C.\|h) | Glucan | Xylan | Glucan | Xylan |
| 120\|1 | 90 | 25 | 92 | 25 |
| 100\|1 | 80 | 42 | 82 | 45 |
| 75\|1 | 72 | 33 | 74 | 35 |

Example III

Poplar and EMIM Acetate at High Biomass Ratios

Poplar was ground and separated to the same sieve cut, incubated in EMIM Acetate, then washed with water. The samples were mixed with IL to form a biomass/IL mixture of varying weight % biomass and incubated without mixing at 120° C. for 1 hour. As seen in FIG. 4, at high weight fractions of biomass to IL there is significant swelling of biomass following uptake of IL.

Enzyme hydrolysis: The procedure for the enzyme hydrolysis is the same as that outlined in Example II.

Results: As seen in Table 6, glucan (cellulose) conversion to glucose is high at all biomass fractions used in pretreatment after 24 hours of enzymatic saccharification.

TABLE 6

Conversion of glucan and xylan to glucose and xylose, respectively, is given for poplar incubated in EMIMAc at varying biomass weight percent. The weight fraction of biomass in the IL-biomass mixture was varied. For 33% weight biomass, glucan conversion to glucose at 48 hour was 89%. For other weight fractions, glucan conversion at 24 and 48 hours was nearly unchanged.

| Biomass | 10 hr Conv. | | 24 hr Conv. | |
|---|---|---|---|---|
| Wt % | Glucan | Xylan | Glucan | Xylan |
| 10 | 86 | 72 | 97 | 76 |
| 20 | 85 | 72 | 92 | 74 |
| 33 | 75 | 55 | 82 | 70 |

Example IV

Poplar and EMIM Propionate or Acetate with High Weight Fraction of Biomass in pretreatment and Saccharification Steps Room Temperature ILs (RTILS) that can process high weight fractions of biomass are of particular value for commercial implementation of the IL-pretreatment technology proposed in this invention. RTILs, being liquids at or near room temperature, have physical properties that allow the conduct of different steps (flow, mixing etc.) of the pretreatment technology easily and economically. Moreover, if the RTIL also has high capacity for disrupting the crystallinity of cellulose, it will be an ideal pretreatment solvent. A "new IL" EMIM-propionate (synthesized by us) and EMIM acetate are representative ILs that meet these requirements. This example documents the performance of these two ILs at high biomass loadings in the pretreatment (33%) and saccharifications steps (10%).

Poplar was incubated in 1-ethyl-3-methyl imidazolium propionate, EMIM Pr, or EMIMAc, then washed with water. The samples were mixed with IL to form a biomass/IL mixture of 33% weight biomass and incubated without mixing at 120° C. for 1 hour.

Enzyme hydrolysis: The procedure for the enzyme hydrolysis is the same as that outlined in Example II except enzyme loadings were 10 FPU/g glucan of cellulase and 60 CBU/g glucan of β-glucosidase with 10 weight % biomass in the saccharification buffer.

Results: As seen in Tables 7 and 8, glucan (cellulose) conversion to glucose is high at the high biomass fractions used in pretreatment and saccharification steps with both ILs.

TABLE 7

Conversion of glucan and xylan to glucose and xylose is given for poplar incubated in EMIM Acetate at 33% by weight biomass.

| Time (h) | Glucan Conv. (%) | Xylan Conv. % |
|---|---|---|
| 12 | 79 | 64 |
| 24 | 75 | 67 |

TABLE 8

Conversion of glucan and xylan to glucose and xylose is given for poplar incubated in EMIM Propionate at 33% by weight biomass.

| Time (h) | Glucan Conv. (%) | Xylan Conv. % |
|---|---|---|
| 12 | 76 | 66 |
| 24 | 83 | 73 |

Example V

Pretreated Poplar Saccharification with Low Enzyme Loadings

Poplar was incubated in EMIMAc and then washed with water. The samples were mixed with IL to form a biomass/IL mixture of 5% weight biomass in IL and incubated with mixing at 120° C. for 30 minutes.

Enzyme hydrolysis: The procedure for the enzyme hydrolysis is the same as that outlined in Example II except that cellulose and β-glucosidase loadings per gram of glucan were varied. The mass of poplar and percent conversion to glucose and xylose was based on the quantity added in the pretreatment step and the sugars content of this quantity.

Results: As seen in Table 9, high conversion of glucan (cellulose) to glucose and xylan (from hemicellulose) to xylose is found after 24 hours of enzymatic saccharification at the low enzyme loadings.

TABLE 9

Conversion of glucan and xylan to glucose and xylose is given for poplar incubated in EMIM Acetate at 5 weight percent. Enzyme loadings were varied and are listed in FPU or CBU per gram of glucan for the cellulase and β-glucosidae, respectively.

| Enzyme loading | 10 hr Conv. | | 24 hr Conv. | |
|---|---|---|---|---|
| FPU\|CBU | Glucan | Xylan | Glucan | Xylan |
| 5\|20 | 62 | 44 | 80 | 58 |
| 5\|60 | 60 | 47 | 89 | 64 |
| 10\|20 | 71 | 45 | 82 | 55 |
| 10\|60 | 83 | 62 | 90 | 68 |

Example VI

Pretreated Biomass of Large Particle Size

Poplar or corn stover biomass was ground and separated to different sieve cut fractions consisting of:
large sized particles of sieve cut +20 (850 μm);
broad sized particles of sieve cuts −20+80 (particle sizes less than 850 μm and greater than 180 μm); and
particles of sieve cuts 40+60 (particle sizes less than 425 μm and greater than 250 μm).

Biomass samples were mixed with EMIM Acetate to form a biomass/IL mixture of 5 weight % biomass and incubated with mixing at 120° C. for 30 minutes. The incubated samples were washed with water prior to enzyme hydrolysis.

Enzyme hydrolysis: The procedure for the enzyme hydrolysis is the same as that outlined in Example II.

Results: The IL pretreatment was effective over a large range of particle size as seen in Table 10, Use of large particles resulted in hydrolysis rates similar to those of more finely ground particles.

TABLE 10

Conversion of glucan to glucose and xylan to xylose for enzyme hydrolysis of poplar and corn stover sample of variable particle size after 9 and 24 hours of saccharification.

| Poplar | | | | | Corn stover | | | | |
|---|---|---|---|---|---|---|---|---|---|
| Sieve | Conv. (9 h) | | Conv. (24 hr) | | Sieve | 9 hr Conv. | | 24 hr Conv. | |
| Fraction | Glucan | Xylan | Glucan | Xylan | Fraction | Glucan | Xylan | Glucan | Xylan |
| +20 | 79 | 59 | 86 | 61 | +20 | 77 | 40 | 90 | 46 |
| −20 + 80 | 77 | 60 | 85 | 65 | −20 + 80 | 79 | 41 | 85 | 43 |
| −40 + 60 | 76 | 63 | 86 | 67 | −40 + 60 | 75 | 37 | 80 | 41 |

Example VII

Effect of Moisture on IL Pretreatment of Biomass

Complete severing of all the hydrogen bonds attaching a cellulose chain to its adjacent chains is the necessary first step in dissolving cellulose from a (semi-crystalline) solid cellulose matrix. It is well-known that the presence of appreciable amounts of dissolved water in an IL interferes with its ability to dissolve cellulose. Water lowers IL's capacity to sever the inter- and intra-chain hydrogen bonds imparting crystallinity to cellulose. While our pretreatment process does not require dissolution of cellulosic portion of biomass in IL, in order to affect its swelling, a few of the cellulosic hydrogen-bonds have to be disrupted. Accordingly, we expect dissolved water to affect IL's performance as a biomass pretreatment solvent.

The admissible water content in IL can affect the economics of the pretreatment method in two aspects. First, it determines how dry the IL has to be before it can be reused. Second, it determines how dry the biomass has to be during incubation with IL. Accordingly, to assess the effect of water content of IL on the effectiveness of our pretreatment technique, in this example we deliberately added various proportions of water to IL prior to incubation of biomass (Table 11) and measured the hydrolysis rates and sugar yields from the resulting pretreated biomass.

Pretreatment: Poplar was mixed with IL and water to form a biomass/IL/water mixtures of 20% weight biomass and different weight % of water (Table 11). The mixture was incubated without mixing at 120° C. for 1 hour in a closed vessel, and then washed with water.

TABLE 11

Incubation of poplar with EMIM Acetate containing different wt % of water. The weights of IL and water were adjusted in these experiments to achieve 20 wt % poplar and 0 to 20% of water.

| Experiment | Poplar (mg) | EMIMAc (mg) | Water (mg) | Moisture % | Pretreatment Time (min) | Pretreatment temperature |
|---|---|---|---|---|---|---|
| 1 | 200 | 800 | 0 | 0 | 60 | 120° C. |
| 2 | 200 | 750 | 50 | 5 | 60 | 120° C. |
| 3 | 200 | 700 | 100 | 10 | 60 | 120° C. |
| 4 | 200 | 600 | 200 | 20 | 60 | 120° C. |

Enzyme hydrolysis: The procedure for the enzyme hydrolysis of the biomass is the same as that outlined in Example II except enzyme loadings were 15 FPU/g glucan of cellulase and 60 CBU/g glucan of β-glucosidase with 5 weight % biomass in the saccharification buffer.

Results: As seen in Table 12, glucan (cellulose) conversion to glucose and xylan conversion to xylose at the end of 24 hrs of hydrolysis remain essentially unaffected until the moisture exceeds well above 10% in the incubation mix. However with incubation mixtures containing moisture at levels of 20% and above, hydrolysis rates appear to slow down and the sugar yields are lower.

TABLE 12

Enzymatic Hydrolysis of poplar incubated in water-laced IL

| | | Enzymatic hydrolysis (Glucan conversions) | | Enzymatic hydrolysis Xylan conversions | |
|---|---|---|---|---|---|
| Experiment | Moisture % | 12 (h) | (24 hrs) | (12 hrs) | 24 (h) |
| 1 | 0 | 92 | 85 | 79 | 78 |
| 2 | 5 | 83 | 82 | 74 | 82 |
| 3 | 10 | 73 | 81 | 75 | 77 |
| 4 | 20 | 39 | 49 | 41 | 50 |

Example VIII

Recovery of IL

The ionic liquid does not irreversibly adsorb onto the biomass and can be completely recovered in the wash solvent at all (low to high) biomass loadings (biomass to ionic liquid weight fractions) used in the incubation step. This example describes the experiments undertaken to establish the amount of IL recovered in the wash solvent following pretreatment of biomass.

TABLE 13

Details of pretreatment experiments (at various biomass loadings) used to establish the recoverability of IL into the wash solvent.

| Biomass loading | Poplar (mg) | EMIMAc (mg) | poplar % | Pretreatment Time (min) | Pretreatment temp | other conditions in pretreatment |
|---|---|---|---|---|---|---|
| low | 250 | 4750 | 5 | 30 | 120° C. | With Mixing |
| medium | 200 | 1800 | 10 | 30 | 120° C. | No mixing |
| high | 300 | 700 | 30 | 60 | 120° C. | No mixing |

In all the cases shown in Table 13, the biomass, following incubation, was contacted with a wash solvent (water or ethanol) for 30 minutes with mixing at room temperature (except the 30% biomass case where the temperature was maintained at 40° C.). The sample was then centrifuged and supernatant was removed and analyzed for ionic liquid (IL) concentration using high performance liquid chromatography with a photodiode array detector. The supernatant is referred to as wash solution and the wash volume was measured. The biomass was washed several times with the wash solvent. The precision of the concentration measurement by chromatography is approximately 2%.

For 5% and 10% poplar in the pretreatment step, results of washings with the ethanol, are given in Tables 14 and 15, respectively. As can be seen from these Tables, very high recovery of IL (close to 100%) in wash solutions are achieved both at 5% (low) and 10% (medium) biomass loadings in the pretreatment step.

TABLE 14

Wash volume, composition, and total weight of recovered ionic liquid using ethanol as the displacement solvent is given below for 5% poplar in the pretreatment step.

| Wash | Concentration (mg/ml) | Volume (ml) | Weight (mg) |
|---|---|---|---|
| 1 | 113.9 | 38.25 | 4357.3 |
| 2 | 8.86 | 37.50 | 332.9 |
| 3 | 0.433 | 38.25 | 16.5 |

Total IL recovered in wash solution, 4706.7 mg, represents 99% recovery.

TABLE 15

Wash volume, composition, and total weight of recovered ionic liquid using ethanol as the displacement solvent is given below for 10% poplar in the pretreatment step.

| Wash | Concentration (mg/ml) | Volume (ml) | Weight (mg) |
|---|---|---|---|
| 1 | 38.6 | 42.5 | 1640.5 |
| 2 | 3.47 | 42.5 | 147.5 |
| 3 | 0.208 | 39.5 | 8.2 |
| 4 | 0.026 | 40 | 1.0 |

Total IL recovered in wash solution, 1797.2 mg, represents 99.8% recovery.

For 30% poplar in the pretreatment step, results of washings with the two solvents, water and ethanol, are given in Tables 16 and 17, respectively. As can be seen from these Tables with either of these wash solvents all the 700 mgs of the IL used in the incubation step were completely recovered.

TABLE 16

Wash volume, composition, and total weight of recovered ionic liquid using water as the displacement solvent is given below for 30% poplar in the pretreatment step.

| Wash | Concentration (mg/ml) | Volume (ml) | Weight (mg) |
|---|---|---|---|
| 1 | 25.55 | 23 | 587.7 |
| 2 | 9.626 | 11.5 | 110.7 |
| 3 | 0.841 | 11.5 | 9.7 |
| 4 | 0.093 | 11.5 | 1.1 |
| | | | Total 709.2 |

Total IL recovered in wash solution, 709.2 mg, represents 100% recovery within the precision of the concentration measurement.

TABLE 17

Wash volume, composition, and total weight of recovered ionic liquid using ethanol as the displacement solvent is given below for 30% poplar in the pretreatment step.

| Wash | Concentration (mg/ml) | Volume (ml) | Weight (mg) |
|---|---|---|---|
| 1 | 24.9 | 24.5 | 609.5 |
| 2 | 7.00 | 11.5 | 80.5 |
| 3 | 0.752 | 12.0 | 9.0 |
| 4 | 0.119 | 11.5 | 1.4 |
| | | | Total 700.2 |

Total IL recovered in wash solution, 700.2 mg, represents 100% recovery within the precision of the concentration measurement.

Example IX

Recycle of IL

Poplar was mixed with EMIMAc to form a biomass/IL mixture of 5 weight % biomass in IL. It was incubated with mixing at 120° C. for 30 minutes, then washed with ethanol three times, followed by two water washes. The IL from the ethanol and water washes was recovered by evaporation of ethanol and water from the extremely low volatility IL. The recovered IL was then used in subsequent biomass pretreatment cycles at constant pretreatment conditions. The water content of the IL was monitored via Karl Fischer titration of samples withdrawn from the recovered IL to ensure that the water content is below acceptable level (see, example VIII). Makeup IL was added (5 to 10% of total IL) after each cycle to compensate for losses due to sampling for water analysis. (This IL loss associated with sampling arises due to the small amount of total IL used in our experiments, and will not be an issue in large scale recycling.) The performance of recycled-IL is compared to that of fresh IL in pre-treating the biomass to establish the least number of cycles up to which the IL retains its effectiveness and can be reused with no additional cleaning steps. The performance of IL can be quantified by one of the two following procedures:

(1) Enzymatic hydrolysis of pretreated biomass (as was done in previous examples) or (2) X-ray powder diffraction (XRD) of the pretreated biomass. The later procedure which is simpler and can be performed rapidly allows one to estimate the crystallinity index, CrI, of the biomass (Segal, L., et al., Text. Res. J., 1959. 29: p. 786-94). We observed that loss in crystallinity of biomass following pretreatment correlates with the enzymatic digestibility (saccharification kinetics) of pretreated biomass.

Enzyme hydrolysis: The procedure for the enzyme hydrolysis is the same as that outlined in Example II.

XRD: Smooth films were cast at room temperature with pretreated biomass on aluminum sample pans. X-ray powder diffraction (XRD) data for these films were generated at 25° C. with an XPERT' PRO powder diffractometer PANALYTICAL with XCELERATOR' detector using Nickel filtered CuKα radiation. Samples were scanned over the angular range 6.0-45.0°, 2θ. From these scans, CrI was estimated.

Native poplar has a measured CrI of about 40 to 50. As seen in Table 18, there is a strong correlation between enzymatic digestibility of the biomass carbohydrates and its CrI.

TABLE 18

CrI and percent conversion of glucan and xylan to monomeric sugars after 24 hours by enzymatic saccharification for poplar pretreated with fresh IL from high to low temperatures. Loss of crystallinity is clearly correlated with increased glucan and xylose conversion.

| Temp | % Conv. (24 h) | | Crystallinity Index |
|---|---|---|---|
| | Glucan | Xylan | |
| High | 97 | 70 | 9 |
| ↓ | 86 | 65 | 18 |
| | 75 | 47 | 36 |
| Low | 42 | 37 | 47 |

Results: Recycled IL produced crystallinity reduction similar to that of fresh IL (Tables 18 and 19). Glucan (cellulose) conversion to glucose following incubation with recycled IL is reported after 36 hours of enzymatic saccharification (Table 20) for a various number of IL-recycles. Conversions over 100% reflect uncertainties in sugar analysis (of 5 to 10%) associated with the refractive index detector method of the high performance liquid chromatography technique.

TABLE 19

The CrI of untreated (native) poplar and samples pretreated with recycled IL (recycle number) indicate that recycled IL is effective in reducing the crystallinity of the biomass sample after repeated recycling. Untreated native poplar has a CrI of 43.

| Recycle number | CrI |
|---|---|
| 0 | 9 |
| 7 | 15 |

TABLE 20

The IL pretreatment of poplar with fresh or recycled IL (Recycle number) indicate that recycled IL is effective in enhancing saccharification of the biomass sample after repeated recycle steps.

| Recycle number | Glucose Conv. % | Xylose Conv. % |
|---|---|---|
| 0 | 100 | 70 |
| 6 | 99 | 59 |
| 9 | 104 | 77 |

Similar results for higher biomass to IL ratios (20%) are shown in Table 21. Here, even after 15 recycles we see no loss in effectiveness of the IL as indicated by the high glucose yields (~90%) at the end of 24 hrs of enzyme hydrolysis of the pretreated poplar. The results on fermentation of the hydrolysate shown in the last column of Table 21 will be discussed in the next example.

TABLE 21

Glucose conversion after 4, 12 and 24 hours on enzyme hydrolysis for poplar pretreated with recycled IL with 20% biomass in the pretreatment step. Ethanol yields are given for 4 hours of fermentation. High glucose conversion was maintained with recycled IL.

| Recycle number | Glucose Conversion (%) | | | Ethanol Yield (%) After 4 hrs of Fermentation |
|---|---|---|---|---|
| | 4 hrs | 12 hrs | 24 hrs | |
| 1 | 84 | 86 | 88 | 50 |
| 13 | 63 | 72 | 86 | 70 |
| 15 | | 73 | 89 | |

Example X

Recovery of Lignin

We carried out NREL recommended LAPS analysis of the solid portion of the biomass (poplar) to identify its cellulose, hemicellulose and lignin proportions at three stages during our pretreatment process: (1) fresh biomass prior to incubation, (2) pretreated biomass after extracting the IL with a wash solvent, and (3) the solid residue left behind after saccharification (enzyme hydrolysis) of the pretreated biomass. By comparing the lignin content of the solids at each of these stages, we concluded that in IL-pretreatment of polar, lignin mainly gets redistributed on the biomass surface and does not dissolve in the IL to any appreciable extent. This redistribution allows the IL to gain access to the hemicellulose and cellulose portions of biomass and swell them. Following saccharification, the residual solid is mainly lignin, and hence filtration of the hydrolysate provides a facile means of recovering the lignin which forms the precursor for a variety of bio-products (see, FIG. 3).

Example XI

Fermentation of Pretreated Poplar to Ethanol using *Saccharomyces cerevisiae*

In this example, we have investigated the fermentation of the hydrolysates obtained following enzymatic hydrolysis of IL-pretreated polar. We did not attempt to subject the hydrolysate to any "conditioning" prior to fermentation to remove potential fermentation inhibitory compounds. We believe that our IL-pretreatment of biomass, which involves incubation of biomass with IL in an almost water-free environment, will not produce compounds commonly seen in other water-based pretreatment methods, such as hydroxymethyl furfural (HMF) and furfural, that inhibit subsequent fermentation of the sugars to alcohol. Also, these fermentation runs confirm that any trace amounts of IL present in the hydrolysate has no adverse affect on the fermentation process. We attempted fermentations on the hydrolysate produced using fresh IL as well as recycled-IL. In principle, some non-volatile extractives from biomass may accumulate in IL recycled several times, when no additional cleaning steps other than water removal are used between each recycle step. The goal is to verify if these accumulated compounds interfere with fermentation in any manner.

Fermentation of hydrolysate obtained following pretreatment with fresh IL with no "conditioning". Poplar was incubated in EMIM Acetate. The samples were mixed with IL to form a biomass/IL mixture of 10 wt % biomass in IL and incubated with mixing at 120° C. for one hour. The pretreated biomass was washed with water to remove all the IL.

Enzymatic hydrolysis: The pretreated biomass was saccharified by enzyme hydrolysis. The procedure for enzyme hydrolysis is the same as that outlined in Example II except that hydrolysis was carried out at varying biomass weight percent of 2, 5 and 10% in the buffer solutions.

Fermentation: Dry bakers yeast (10 g/l) in the form of *Saccharomyces cerevisiae* (Type II, Sigma Aldrich) was used. Yeast was added after 24 hrs of enzymatic hydrolysis of poplar. The final yield of ethanol was calculated based on initial sugars in biomass. Fermentation was carried out at a temperature of 34° C. and 130 rpm in an incubator shaker. The ethanol yields obtained after fermentation are shown in Table 22. The yield of ethanol remained constant after 9 hrs for 2 and 5% and after 24 hrs for 10% poplar loadings. Yields from enzymatic hydrolysis are close to theoretical (see column 2, Table 22).

TABLE 22

Glucose conversion is measured after 24 hours of enzyme saccharification followed by fermentation. Ethanol yields from sequential hydrolysis and fermentation of EMIMAc pretreated poplar after nine hours of fermentation (2 and 5% poplar) or 24 hrs of fermentation (10% poplar).

| Percent Biomass in Saccharification | Glucose Conv. (%) | Ethanol Conv. (% l) |
|---|---|---|
| 2 | 100 | 92 |
| 5 | 102 | 76 |
| 10 | 84 | 73 |

Fermentation of hydrolysate obtained following pretreatment with recycled-IL with no "conditioning": Fermentation of the hydrolyzate was assessed by adding 10 mg/ml of bakers yeast to hydrolyzates and sampled after four hours of fermentation at 30° C. Ethanol yield was calculated based on glucose available from glucan in the poplar samples. The resulting yields are shown in the last column of Table 21 (previous example). As can be seen from Table 21, even after 13 cycles of reuse of IL, the ethanol yields are almost the same as those seen with the runs that used fresh IL (Table 22). The data in Tables 21 and 22 also confirms that any traces of IL left behind in the IL have no adverse affect on the fermentation.

Example XII

Fermentation of IL-Pretreated Poplar Hydrolysate to Lactic Acid using *Lactobacillus Casei*

Poplar was incubated in EMIM Acetate. The samples were mixed with IL to form a biomass/IL mixture of 30 wt % biomass in IL and incubated without mixing at 120° C. for one hour. The pretreated biomass was washed with water to remove all the IL.

Enzymatic hydrolysis: The pretreated biomass was saccharified by enzyme hydrolysis. The procedure for enzyme hydrolysis is the same as that outlined in Example II except that hydrolysis was carried out at 10% in the buffer solutions. The glucose content (determined by HPLC) in the saccharified solution was 20 mg/ml.

Bacterial Strain and Media: *Lactobacillus Casei* was purchased from ATCC and grown according to protocol provided. The cells were grown in MRS broth (Becton Dickinson) as well as on MRS agar plates with robust growth. The strain was maintained on Agar plates at 4° C.

Media Preperation: The control media solution was also prepared in 50 mM Citrate buffer pH 4.8. The components in the media were peptone 10 g/l, beef extract 10 g/l, yeast extract 5 g/l, glucose 20 g/l, polysorbate 80 1 g/l, sodium acetate 5 g/l, magnesium sulfate 0.1 g/l, manganese sulfate 0.05 g/l, and potassium phosphate dibasic 2 g/l. The pH was adjusted to 6.5 with ammonium hydroxide. The solution was either filter sterilized or autoclaved at 121° C. for 30 minutes. The biomass media solution was prepared in the exact same manner, except no glucose was added to the solution.

Fermentation Conditions: All experiments were carried out in shake flask, at 37° C. and 150 rpm on a shaking incubator. The inoculum was prepared by transferring the bacterial strain from the agar plate to the shake flask and allowing it to incubate for 20 hrs. Fermentation flasks received 20% inoculum volume.

Analytical Methods: Lactic acid concentration and glucose concentration was determined by HPLC equipped with an RI detector and a UV detector at 210 nm. An organic acid column (Biorad HPX-87H) was used with 5 mmol $H_2SO_4$ as the mobile phase at a flow rate of 0.4 ml/min, and the column was maintained at 65° C. Cell density was determined by measuring the absorbance at 600 nm with a UV-Vis spectrophotometer.

Results:

|  | Control | | Biomass | |
|---|---|---|---|---|
| Time (hrs) | OD 600 nM conc. | Lactic acid (mg/ml) | OD 600 nm conc. | Lactic acid (mg/ml) |
| 0 | 0.6 | 0 | 1.8 | 0 |
| 3 | 1.1 | 1.5 | 3.0 | 3 |
| 11 | 0.95 | 6 | 6.1 | 15 |
| 24 | 0.86 | 6 | 7.0 | 22 |
| 32 | 0.67 | 7 | 7.4 | 24 |

Lactic acid yield was 35% for control solution. There is no robust growth in the shake flask. However, in the seed flask robust growth was always observed with the maximum OD at 4.0 and a lactic acid yield of 50%.

Lactic acid yield for biomass solution is 100%. There was robust growth seen in shake flask as well as in the seed flask. An OD of 9.5 was observed in the seed flask with lactic acid yield being 100%. Such high conversions indicate that the bacterial strain is capable of using other sugars (besides glucose) hydrolyzed from the biomass. Xylose was monitored and was not consumed during the fermentation.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

In another embodiment, the steps of incubating the biomass in an ionic liquid (IL) for a sufficient time at an appropriate temperature to remove or redistribute a substantial portion of the lignin so that the IL is able to penetrate the hemicellulose as well as the crystalline cellulose buried in the hemicellulose and swell these structures significantly. The significant swelling broadly is at least 20% swelling and preferably at least 30%. The swelling, however, may vary widely. The swelling may be 20 to 300% swelling; 30 to 200% swelling or 30 to 100% swelling. Typically, the swelling ranges from 30 to 50%.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A method for treating a lignocellulosic biomass comprising the steps of: incubating a lignocellulosic biomass comprising lignin, cellulose, and hemicellulose in an ionic liquid (IL) for a sufficient time and temperature to swell the cellulose and hemicellulose by without dissolution of the biomass in the IL; washing the IL-incubated biomass comprising lignin, cellulose and hemicellulose with a liquid non-solvent for cellulose that is miscible with water and the IL; and contacting said swelled washed biomass comprising lignin, cellulose and hemicellulose with an aqueous buffer comprising enzymes capable of hydrolyzing both cellulose and hemicellulose to produce polysaccharides, and converting said polysaccharides to hexose and pentose sugars.

2. A method according to claim 1 wherein said contacting step forms a post-saccharification solid residue comprising lignin.

3. A method according to claim 2 wherein the lignin can be converted to fuels, chemicals, or polymers.

4. A method according to claim 1 comprising the further step of converting the hexose and pentose sugars to fuels, chemicals, or polymers.

5. A method according to claim 3 wherein between 75% to 97% of the cellulose is converted to glucose after 24 hours.

6. A method according to claim 1 wherein the time and temperature during the step of IL-incubation of the biomass is optimized to sufficiently swell matrices of the biomass to enhance the penetration of hydrolyzing enzymes and water during the hydrolysis step.

7. A method according to claim 1 wherein the incubating step comprises incubating the biomass for a time ranging from 5 minutes to 8 hours at a temperature ranging from 50° C. to 200° C.

8. A method according to claim 1 wherein the ionic liquid is molten during incubation.

9. A method according to claim 1 wherein the IL is capable of disrupting hydrogen-bonding in the structure of the cellulose or the hemicellulose wherein the IL comprises a cation selected from imidazolium, pyrrolidinium, pyridinium, phosphonium, or ammonium.

10. A method according to claim 1 wherein the IL is represented by the structure:

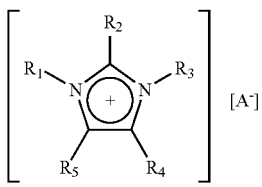

wherein each of R1, R2, R3, R4, and R5 is hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein $A^-$ is a halide, hydroxide, formate, acetate, propanoate, butyrate, any mono- or di-carboxylic acid having up to a total of 10 carbon atoms, succinate, lactate, aspartate, oxalate, trichloroacetate, trifluoroacetate, dicyanamide, or carboxylate.

11. A method according to claim 1 wherein the IL is represented by the structure:

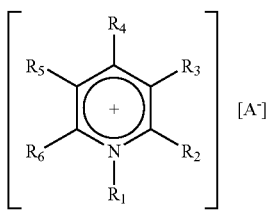

wherein each of R1, R2, R3, R4, R5, and R6 is hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein $A^-$ is a halide, hydroxide, formate, acetate, propanoate, butyrate, any mono- or di-carboxylic acid having up to a total of 10 carbon atoms, succinate, lactate, aspartate, oxalate, trichloroacetate, trifluoroacetate, dicyanamide, or carboxylate.

12. A method according to claim 10 or 11 wherein the halide is a chloride, fluoride, bromide or iodide.

13. A method according to claim 1 wherein the IL is 1-n-butyl-3-methylimidazolium chloride, 1-allyl-3-methyl imidazolium chloride, 3-methyl-N-butylpyridinium chloride, 1-ethyl-3-methyl imidazolium acetate, or 1-ethyl-3-methyl imidazolium propionate.

14. A method according to claim 1 wherein the liquid non-solvent for cellulose that is used for washing is water, an alcohol, acetonitrile or a solvent which dissolves the IL and thereby extracts the IL from the biomass.

15. A method according to claim 14 wherein the alcohol is ethanol, methanol, butanol, or propanol, and wherein the IL is recovered from the liquid non-solvent.

16. A method according to claim 15, comprising the further step of reusing the recovered IL for treating more biomass.

17. A method according to claim 15, comprising recovering the IL from the liquid non-solvent by a method selected from one or more of activated charcoal treatment, distillation, membrane separation, electro-chemical separation techniques, sold-phase extraction and liquid-liquid extraction.

18. A method according to claim 1, wherein the biomass is corn stover or poplar, and wherein the time required for complete enzymatic hydrolysis is within 16 to 36 hours.

19. A method according to claim 1, wherein the ionic liquid has a water content not exceeding 10%.

20. A method according to claim 1 wherein the incubation temperature is achieved by heating with agitation or microwave irradiation with intermittent agitation.

21. A method according to claim 1 wherein the ionic liquid is a mixture of composition described by Equation 1:

$$\sum_{n=1}^{20} [C^+]_n [A^-]_n$$

wherein $C^+$ denotes a cation of the IL and $A^-$ denotes an anionic component of the IL and further wherein each additional IL added to the mixture may have either the same cation as a previous component or the same anion as a previous component, or differ from the first only in the unique combination of the cation and anion.

22. A method according to claim 21, comprising a five component mixture of the following ILs: 1-butyl-3-methyl imidazolium chloride ([BMIM$^+$][Cl$^-$])+1-butyl-3-methyl imidazolium hexafluorophosphate ([BMIM$^+$][PF$_6{}^-$])+1-ethyl-3-methyl imidazolium chloride ([EMIM$^+$][Cl$^-$])+1-ethyl-3-methyl imidazolium hexafluorophosphate ([EMIM$^+$][PF$_6{}^-$])+1-ethyl-3-methyl imidazolium tetrafluoroborate ([EMIM$^+$][BF$_4{}^-$]).

23. A method according to claim 1, comprising the further step of recovering the IL following the washing step.

24. A method according to claim 23, wherein 99% or more of the IL is recovered.

25. A method for disruption of the structure of a lignocellulosic biomass which comprises lignin, cellulose and hemicellulose and treating the disrupted biomass, comprising the steps of:
  incubating the biomass in an ionic liquid (IL) for a sufficient time and temperature to swell the cellulose and hemicellulose without dissolution of the biomass in the IL; washing the swelled IL-incubated lignocellulosic biomass with a liquid non-solvent for cellulose that is miscible with water and the IL; and
  treating the incubated and washed lignocellulosic biomass with chemical or biochemical reagents to effect the conversion of the swollen biomass to useful chemicals.

26. A method according to claim 25 wherein the biochemical reagent used to convert the washed biomass is an added enzyme.

27. A method according to claim 25 wherein the treating step comprises adding a buffer comprising enzymes capable of hydrolyzing both cellulose and hemicellulose to the incubated and washed biomass to hydrolyze the cellulose and hemicellulose to sugar.

28. A method according to claim 1 or claim 27 wherein the aqueous buffer comprising enzymes comprises an enzyme mixture of cellulases, endo-glucanases, exo-glucanases, and 1-β-glucosidases.

29. A method according to claim 28, comprising the further step of recovering the enzymes from the hydrolyzed biomass.

30. A method according to claim 28, wherein said enzyme mixture further comprises xylanases or arabinases.

* * * * *